United States Patent [19]

Winstead et al.

[11] Patent Number: 5,565,981
[45] Date of Patent: Oct. 15, 1996

[54] INTERIOR INSPECTION METHOD AND APPARATUS FOR ENCLOSED SPACES

[75] Inventors: Richard W. Winstead, Bridge City; Robert L. Mitchem, Crosby, both of Tex.

[73] Assignee: Rescar, Inc., Downers Grove, Ill.

[21] Appl. No.: 544,472

[22] Filed: Oct. 18, 1995

Related U.S. Application Data

[63] Continuation of Ser. No. 208,687, Mar. 11, 1995, abandoned.

[51] Int. Cl.$^6$ .................................................. G01N 21/88
[52] U.S. Cl. .................................................. 356/241
[58] Field of Search ..................... 356/241, 237, 356/378; 15/324, 339; 73/151; 250/256; 348/45, 65, 68, 85; 385/116, 117; 128/4–11, 17

[56] References Cited

U.S. PATENT DOCUMENTS

| | | | |
|---|---|---|---|
| Re. 31,074 | 11/1982 | Nolte | 356/241 |
| 4,078,864 | 3/1978 | Howell | 356/241 |
| 4,317,632 | 3/1982 | Orphan et al. | 356/241 |
| 4,651,201 | 3/1987 | Schoolman | 358/98 |
| 4,672,437 | 6/1987 | Casper | 356/241 |
| 4,830,491 | 5/1989 | Grace | 356/241 |
| 4,974,168 | 11/1990 | Marx | 356/241 |

FOREIGN PATENT DOCUMENTS

| | | | |
|---|---|---|---|
| 1123366 | 9/1956 | France | 356/241 |
| 0169746 | 9/1985 | Japan | 356/241 |

*Primary Examiner*—Hoa Q. Pham
*Attorney, Agent, or Firm*—Richard J. Myers; Edward D. Gilhooly

[57] ABSTRACT

An inspection apparatus for viewing and making video recordings of the interior of an enclosed space of an enclosure having an elongated body. A pair of housings are mounted on the lower end of the elongated body and respectively contain a light source for illuminating an area of the enclosed space and a video camera for creating an image of the illuminated area of the enclosed space. The video camera includes a video magnetic tape media for recording the images illuminated by the light source. A television monitor is mounted on the upper portion of the elongated body for simultaneously viewing the images created by the video camera.

13 Claims, 3 Drawing Sheets

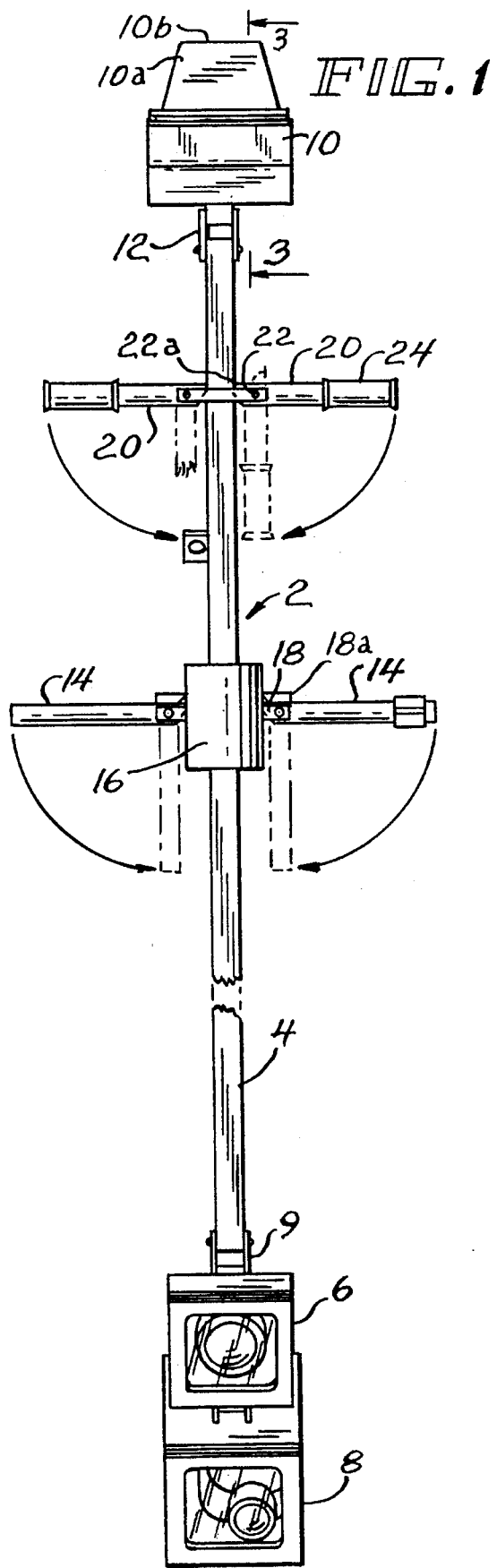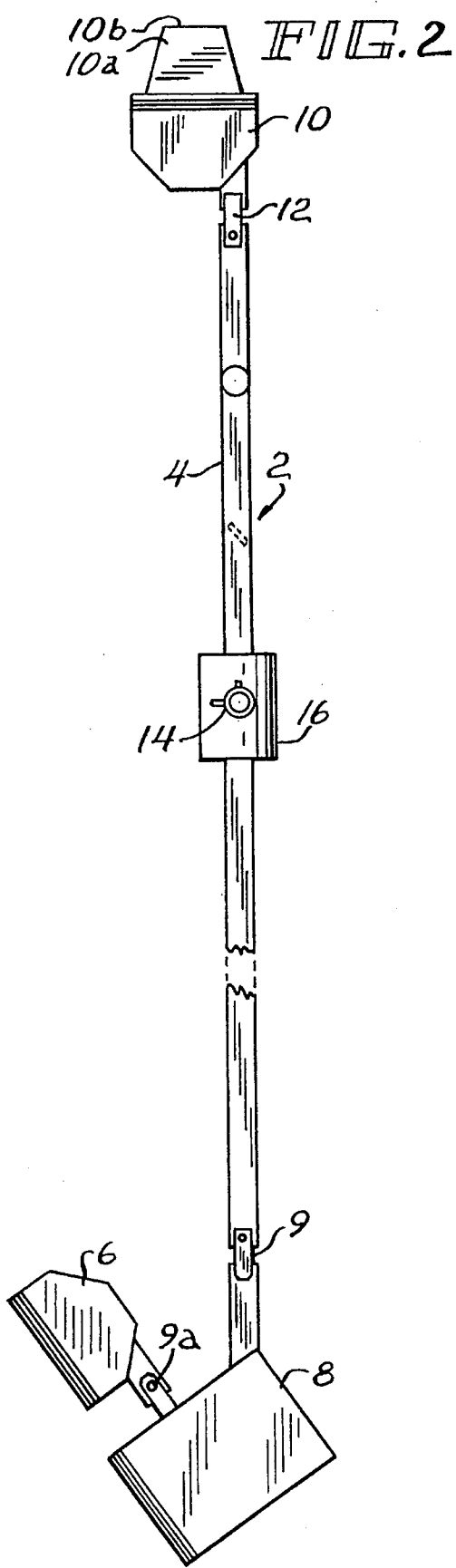

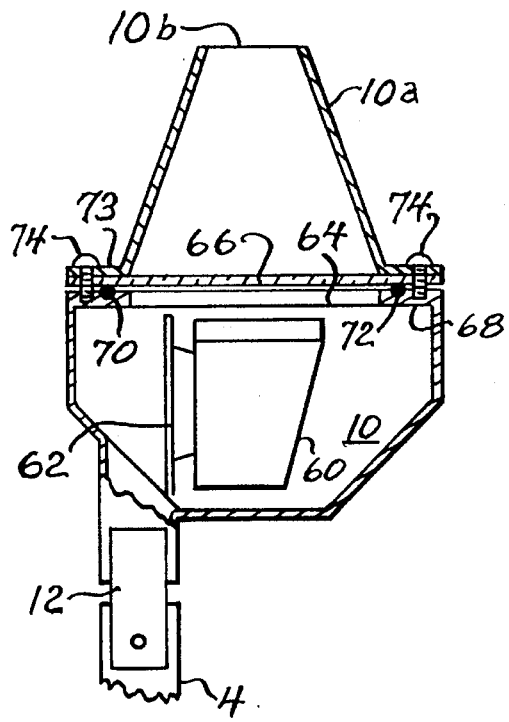
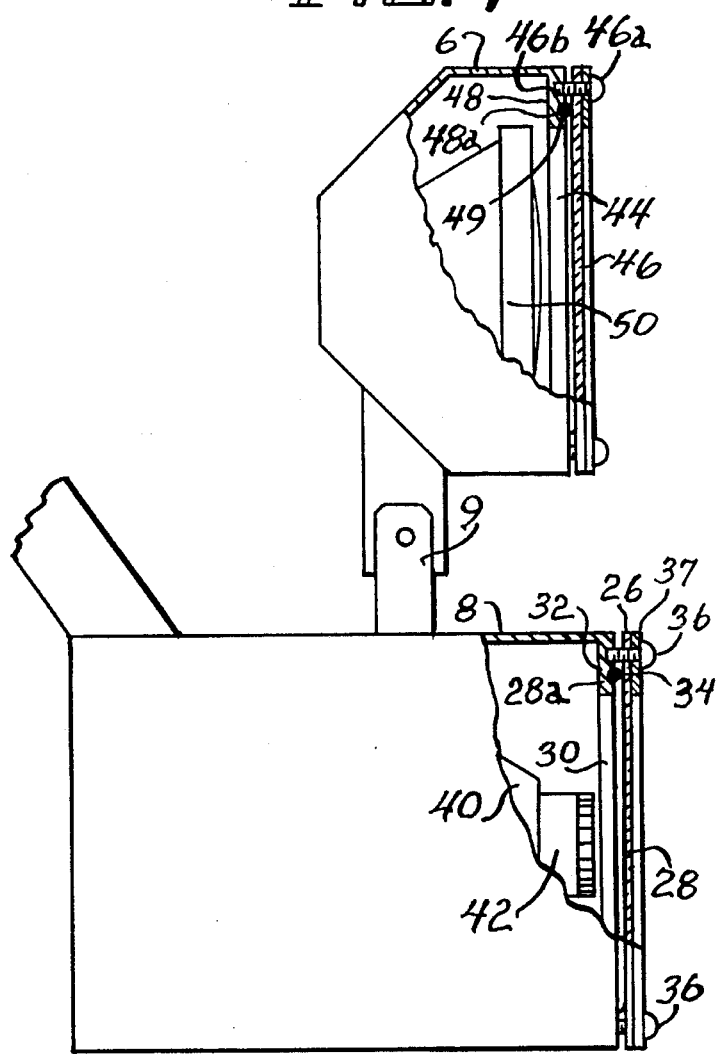

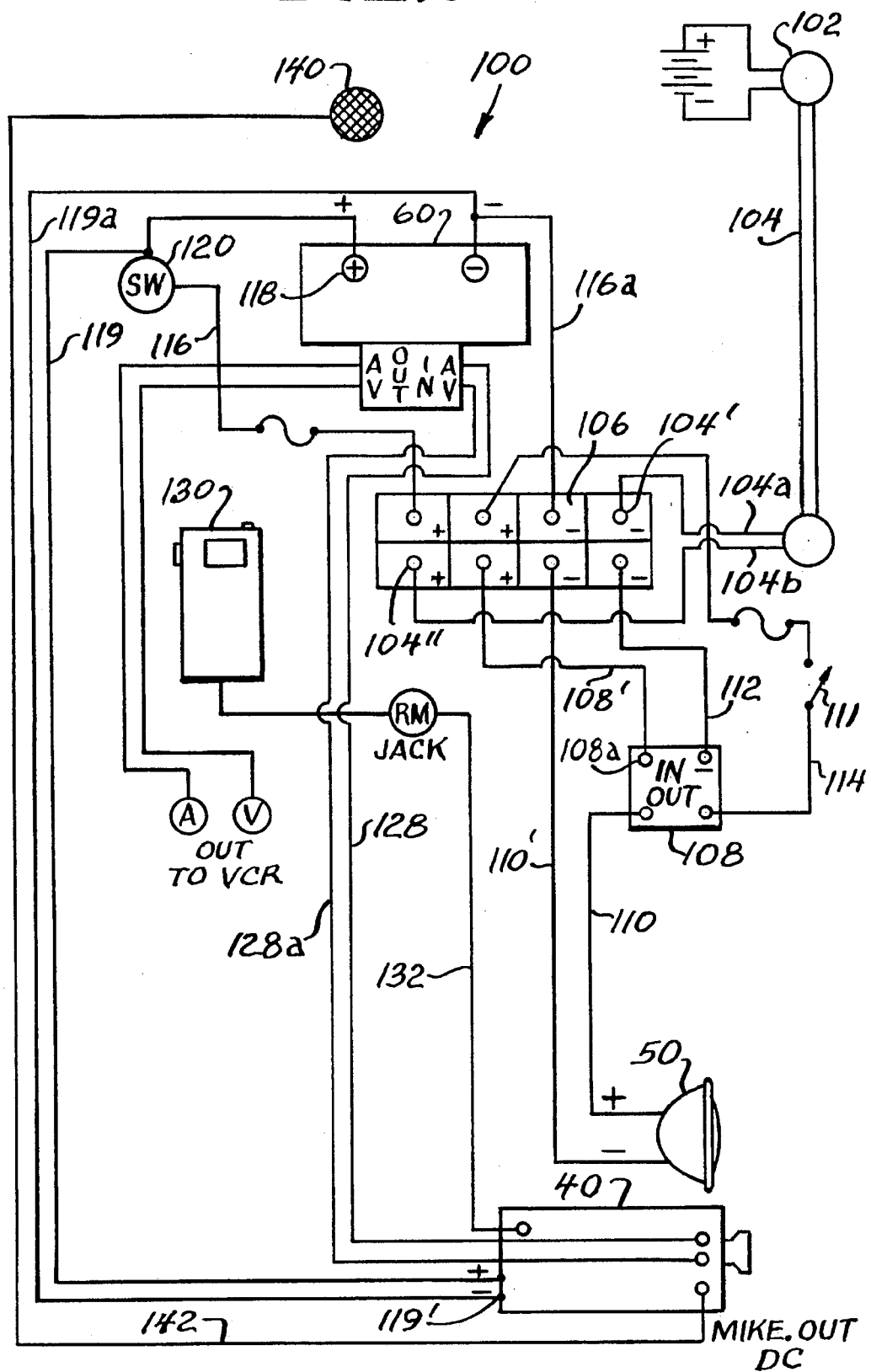

INTERIOR INSPECTION METHOD AND APPARATUS FOR ENCLOSED SPACES

This is a continuation of application Ser. No.208,687 filed Mar. 11, 1995, abandoned.

BACKGROUND OF THE INVENTION

1. Field of the Invention

This invention relates to an inspection method and apparatus for enclosed spaces and more particularly, to an interior inspection apparatus and method for tanks and vessels, such as on rail cars, and other enclosed spaces.

2. Description of the Prior Art

A significant problem exists in industry for satisfactorily inspecting enclosed internal spaces that transport or store a multitude of different chemicals, petroleum products, and other substances. Many liquids stored in a tank or vessel may be toxic and corrosive, and can be hazardous to humans. Prior to introducing these substances into a vessel or tank, it is desirable to inspect the interior of the tank or vessel to evaluate its suitability for continued use and determine whether repairs or other servicing is required for safe storage and/or transport of the substances. Such inspections are needed to consider numerous conditions within the vessel or tank prior to cleaning, repairing, or filling. The vessel or tank should be inspected for overall quality assurance of the structure and verify the level of corrosion and the like within the interior. During these inspections, the physical integrity of the lining of the tank can be evaluated as well as the status of any coils or other appurtenances that may be present within the confined space.

In many cases, it is necessary to make a residue measurement prior to cleaning or filling the vessel and otherwise generally inspect the enclosed space for safe pre-cleaning. This inspection of the interior of tanks or hoppers is particularly necessary for safe operation of rail cars which transport a host of chemicals and other products that can be hazardous to humans or the environment, if not safely contained within the rail car.

Because of the size and configurations of large vessels or tanks in the field, it is extremely difficult to gain access to the interior of the enclosed space for an adequate inspection. In addition, it can be unsafe for an individual to enter into the enclosed space even when access is possible, due to the potentially dangerous nature of the materials that were stored or transported in the vessel or tank.

In the past, internal inspections have been made either by physical entry or by various types of optical equipment, such as periscopes and the like. Such known techniques of visualizing the condition of an enclosed space are not optimumly satisfactory in providing an inspector with a complete visualization of the condition of the interior and are not capable of providing a permanent visual and audio record for later reference. The attainment of effective visualization of the interior of a vessel a tank, or any other confined space is an important need in the industry for reasons of economy, safety, sustained service of the equipment, and proper subsequent handling of materials being transported or stored. Accordingly, it is desirable in the prior art to provide an improved visual inspection method and apparatus for effectively viewing and evaluating the physical condition of the interior of a confined space.

SUMMARY OF THE INVENTION

It is therefore an objective of the present invention to provide an improved interior inspection method and apparatus for inspecting the physical condition of the interior of tanks, vessels, or other enclosed spaces in which a variety of chemicals, liquids, and the like are stored, transported or otherwise handled, or into which access for inspection is limited because of physical constraints. The invention of the application is particularly effective in allowing for the periodic inspection of the tanks of rail cars and other vehicles. The inspection device herein disclosed is readily handled and operated by a single operator, is compact in design, and is easy to use. The invention of the application includes a housing that is inserted into the hatch or access opening of the confined space and includes an effective lighting source capable of illuminating all areas of the tank as the housing is manipulated. The imaging system utilizes a video tape system in which the operator may view the interior with great effectiveness and make audio observations and record images of the interior for later reference. The imaging system of the invention can be operated safely by an individual without exposure to potentially unsafe conditions which may exist within the interior of the vessel or tank.

The imaging system not only is highly effective in inspecting the interior of a tank, vessel, or hopper of a rail car or other vehicle, but can be used to view the interior of any enclosed space that may be inaccessible or hazardous, or is an enclosed space that requires periodic maintenance and control. Efficient inspections can be made by the invention by an operator situated exteriorly of the enclosed space for safety and ease of operation.

During inspections, the quality of the walls and lining of the enclosed space can be evaluated by the invention for structural integrity, corrosion levels, material residue, and the like prior to cleaning or repair, or loading. Subsequent to cleaning, the effectiveness of a cleaning or repair operation can also be evaluated by the invention herein disclosed. The inspection method and apparatus are also useful to review the quality of coils or other devices that may be present in the confined space.

BRIEF DESCRIPTION OF THE DRAWINGS

FIG. 1 is a front elevational view of the interior inspection apparatus of the invention;

FIG. 2 is a side elevational view of the interior inspection apparatus of FIG. 1;

FIG. 3 is a partial side view, with parts in section, taken along lines 3—3 of FIG. 1;

FIG. 4 is a partial side view, with parts broken away in section, of the interior inspection apparatus of FIG. 1 showing the light source and video camera housing of FIG. 1; and FIG. 5 is schematic illustration of the electrical control circuit of the imaging apparatus of FIG. 1.

DESCRIPTION OF THE PREFERRED EMBODIMENT

Referring to FIG. 1, there is illustrated the imaging apparatus 2 of the invention for inspecting and evaluating the condition of the interior of a vessel, tank, or other enclosed space into which access is limited or presents hazardous conditions. The imaging apparatus 2 includes an elongated hollow housing 4 constructed from a suitably rigid material, such as aluminum, plastic, and the like. The elongated housing 4 is intended to be inserted through an access opening (not shown) of a tank, vessel, or other confined space, such as through the coaming of a railway tank car or hopper. A sealed light housing 6 and a video camera/recorder housing 8 are affixed by a threaded latch assembly 9 to the bottom of housing 4. The latch assembly 9 permits the video camera/recorder housing 8 to be pivotally adjusted relative to the axis of housing 4 and be fixed at a selected position. The light housing 6 is mounted on the video camera/recorder housing 8 by a threaded bracket assembly 9a to permit pivotal movement for selective adjustment and includes a threaded member that can be tightened to position light housing 6 at a fixed selected position.

A monitor receptacle 10 and viewing hood 10a are affixed by threaded bracket assembly 12 to the upper end of the housing 4. As seen in FIG. 3, the hood 10a is in the form of a truncated cone having an open end 10b through which the interior of monitor housing 6 can be clearly viewed in the presence of glare from sunlight or bright lights. The threaded bracket assembly 12 permits the monitor housing 10 to be pivotally adjusted and fixed at a convenient viewing position relative to housing 4.

An opposed pair of pivotal support arms 14 (FIGS. 1 and 2) are affixed for swiveling movement as shown in phantom (in FIG. 1) on a cylindrical support 16 which is suitably affixed to the elongated housing 4. The support arms 14 are attached to cylindrical support 16 by brackets 18 having an upper portion 18a. The upper portion 18a creates an engagement area that bears against the cylindrical member 16 in an outward position of support arms 14 for supporting the housing 4 while extending into a vessel or tank. For example, the support arms 14 engage the top of the coaming of a hopper car tank to vertically support housing 4 while it extends into the tank and positions the light housing 6 and video camera/recorder housing 8 within the confined space for an inspection of its interior. The support arms 14 can be folded against the housing 4 for convenient transport of the inspection apparatus 2 (in phantom in FIG. 1). A pair of opposed handles 20 are pivotally mounted above the support arms 14 by brackets 22. The handles 20 can be folded flat against housing 4 for transport as shown in phantom in FIG. 1. An upper portion 22a of brackets 22 engages housing 4 in an outward position of handles 20 and prevents further upward movement of the handles 20. The handles 20 have grips 24 at each end to enable an operator to manipulate and rotate the housing 4 during an inspection of the interior of the tank or other vessel being viewed.

As best seen in FIG. 4, video camera/recorder housing 8 includes a cover plate 26 having a sealed lens cover 28 fabricated from Lexan or similar lens material to enclose opening 30 of housing 8. The lens cover 28 is sealed through the use of an O-ring groove 28a formed in annular flange 32 surrounding opening 30. An O-ring 34 is compressed into the groove 28a by cover plate 26 being affixed to housing 8 by a plurality of screws 36 extending through ring 37. Housing 8 encloses a conventional video camera/recorder 40 in a sealed environment. An example of a commercially available video camera/recorder that is suitable in the invention of the application is sold under the trademark SONY as a Model TR-31 8 mm camera recorder having a ten power magnification fitted with a 2× telephoto lens 42 bringing the magnification capability up to 20×. It is desirable that the telephoto lens 42 also have a circular polarizer effect lens to reduce glare from the light emanating from light housing 6.

The light housing 6 is also includes an opening 44 that is enclosed by a sealed lens cover 46, such as a Lexan lens. As seen in FIG. 4 the lens cover 46 is affixed by threaded member 46a and O-ring 46b to a flange 48 surrounding opening 44. An O-ring 48a is mounted in groove 49 formed in flange 48 to seal the interior of the light housing 6. A light source 50 is mounted within light housing 6 by a suitable mounting (not shown) to illuminate the areas being inspected by the video camera/recorder 40. Although any suitably bright light source 50 may be used, a commercially available light source, namely a General Electric, Part No. 4509 dual filament sealed beam unit, is provides efficient results in the operation of the invention. The light produced by the light source 50 produces a narrow beam giving it the ability to penetrate total darkness in the tank of a rail car or other enclosed space. In use of interior inspection apparatus 2, highly satisfactory illumination has been attained by having the image of the video camera/recorder 40 being directed above the light beam of light source 40 in a slight criss-crossing path for enhanced viewing of the interior. The Lexan glass lens covers of both the light housing 6 and the video camera housing 8 are capable of withstanding high temperatures and exhibit high resistance to many different types of chemicals which may exist within the environment of the tank or vessel.

As seen in FIG. 3, a color video monitor 60 is suitably mounted on a support bracket 62 within the monitor housing 10. The monitor housing includes an opening 64 covered by a lens cover 66, such as a Lexan lens, in alignment with the viewing screen of monitor 60. The monitor housing 10 also includes a cylindrical flange 68 having a continuous groove 70 to receive an O-ring 72 for sealing. The O-ring 72 presses against the interior of the lens cover 66, while the hood 10a is mounted in sandwiched relationship with the lens. The hood 10a includes a peripheral flange 73 through which a plurality of threaded members 74 extend to seal the interior of monitor housing 10.

Referring to FIG. 5, there is illustrated the control circuit 100 for the interior inspection apparatus 2 of the invention. The interior inspection apparatus 2 is electrically energized by a rechargeable 12 volt battery 102 which powers the monitor 60, light source 50 and video camera 40. The battery 102 is electrically connected to the circuit of the inspection apparatus 2 by an elongated electrical cable 104, which may be approximately 20 feet in length, such that the heavy battery may remain on the ground surface during an inspection operation. The leads 104a, 104b of cable 102 are attached to terminals 104', 104" of a double, row six circuit terminal block 106 such as, or example, a commercially available terminal block, PART #750–4307 sold by Allied Electronics.

The "in" terminal 108a of a 12 volt, 30 ampere relay, 108, such as a commercially available relay, PART #275–226 sold by Radio Shack, is connected by lead 108' to a positive terminal of block 106. The output of the relay 108 is connected to the positive terminal of the light source 50 through electrical lead 110. The negative terminal of light source 50 is connected to the block 106 by lead 110'. Negative terminals of terminal block 106 and relay 108 are connected by lead 112. Operation of the light source 50 is activated and/or deactivated by power switch 114a connected to line 114 between positive terminals of relay 108 and terminal block 106. A pair of leads 116, 108a are respectively connected between plus and minus terminals of the terminal block 106 and the plus and minus terminals of monitor 60 having a 12 volt to 6 volt power converter 118, such as, for example, a commercially available Tundra VRL-18 12 volt to 6 volt power converter.

Leads 119, 119a connect terminal block 6 to the video camera 4 through a 12 volt to 6 volt power converter 119' of the same type as converter 118.

A switch 120 is present in lead 116a to control on/off power from terminal block 6 to video camera/recorder 40 and TV monitor 60 respectively through leads 124, 124a and leads 126, 126a. The A-V output of video camera 40 is applied through the input to the monitor 60 through leads 128, 128a. A wired remote control operator 130 is connected through lead 132 to video operation to control its operation. The wired remote operator 130 may be a commercially available Sony RM-95 remote commander. A microphone 140, which can be exteriorly oriented adjacent to the operator at the hood 10a during inspection, is attached by a jack through lead 142 to the video camera 40 and permits the operator to make verbal observations during visualization of the interior for recording on the video tape. Thus, it should be apparent that the video camera 50, having a magnification capability of 1×to 20×under the illumination of the sealed beam, permits an operator to visualize the interior through manipulation of the device 2 while recording the image on video tape (not shown) with verbal observations being recordable through microphone 140. The remote commander provides numerous control features of the camera as are conventional to allow for proper visualization for enhanced results and quality assurance. The control circuit 100 acts to activate and control operation of the monitor 60, light source 50 and video camera 40. The voltage from battery 102 applies power to the various components of the control circuit. The block 106 applies the voltage to the relay 108 which is a standard relay to supply a 12 volt, 30 ampere current to operate the light source 40. The light source is independently activated and deactivated by power switch 114a. Another output of terminal block 106 is supplied through leads 116, 106a to a 12 volt to 6 volt power converter 118 mounted on the monitor 60 to energize operation of the monitor in its sealed position within the housing. Similarly, lines 119, 119a control operation of the video camera 40 through a 12 volt to 6 volt power converter 119' of the same type as converter 118. Power to the monitor 60 and the video camera 40 is activated by switch 120. Operation of the video camera 40 within the enclosed environment is controlled by the individual operator by wired remote operator 130 to control the normal functions of video camera 40 in a manner well known in the art, such as, for example, the lens position, start and stop operation of the camera, zoom, record mode, playback mode, and the like.

What is claimed is:

1. A portable inspection apparatus for viewing the interior of an enclosed space of a structure through an access opening comprising:

body means including an elongated rigid housing having a lower end portion and an upper end portion, said rigid housing capable of being manually manipulated by an individual, said lower end portion of said body means being arranged to be inserted into the enclosed space through an access opening, said upper end portion being arranged to be positioned exteriorly of the access opening of the enclosed space, support means being affixed to said elongated rigid housing, said support means supporting said body means on the structure with said lower end portion inserted through the access opening into the enclosed space, lower housing means being affixed to said lower portion of said elongated rigid housing, said lower housing means having a light source directing a light beam to illuminate selected areas of said enclosed space, said lower housing means further having a video camera means for creating an image of said selected areas illuminated by said light source, viewing means being mounted in the upper end portion of said rigid housing, said viewing means enclosing a video monitor in said rigid housing, said video monitor being operatively connected to said video camera means and being exteriorly arranged from said enclosed space for viewing the image created by said video camera means, and said lower housing means forming an enclosure to seal said light source and said video camera means, said video camera means including a video camera for recording images on a magnetic tape media.

2. The apparatus according to claim 1 wherein said support means includes a pair of pivotable arms, said pivotable arms being moveable to an outward position to engage the structure for supporting said body means with said lower portion inserted into said enclosed space.

3. The apparatus according to claim 2 wherein said body means further includes handle means mounted on said elongated rigid housing above said support means, said handle means being arranged to permit said rigid housing to be manually manipulated to illuminate and create an image of a plurality of areas within said enclosed space.

4. The apparatus according to claim 1 wherein said upper end portion of said rigid housing includes a hood, said hood having open areas for viewing said monitor without glare from external lighting.

5. The apparatus according to claim 1 further including microphone means being positioned exteriorly of said enclosed space and being operatively connected to said video camera means, said microphone means permitting audio recordings on the magnetic tape recording the images in said video camera.

6. The inspection apparatus according to claim 1 wherein said enclosure formed by said lower housing means includes a first housing for sealing said light source and a second housing for sealing said video camera, said first housing and said second housing being connected.

7. The apparatus according to claim 6 wherein said first housing is mounted on said second housing for adjustable movement.

8. The apparatus according to claim 7 wherein said lower housing means is mounted on said lower portion for selected adjustable movement.

9. A method of inspecting the physical condition of the interior of an enclosed structure comprising the steps of positioning an elongated housing partially through an access opening of the enclosed structure with a lower end being within the enclosed structure an upper end being exteriorly of the enclosed structure and aims bearing on the enclosed structure, directing a light beam from a light source on the housing in the enclosed structure toward selected areas of the interior of the enclosed structure for viewing, creating images from the housing within the enclosed structure of said selected areas by a video camera to provide a visualization of the condition of the interior, recording said images on a recording medium, visually monitoring said images through a video monitor pivotally mounted on the housing externally of the enclosed structure, and manipulating said housing from exteriorly of the enclosed structure to change areas illuminated by said light beam.

10. The method of claim 9 further comprising the step of maintaining said light source and said camera in a sealed housing within the interior of the enclosed structure.

11. The method of claim 9 wherein said step of creating images of said selected areas by a camera is through use of a magnetic video camera/recorder.

12. The method of claim 11 wherein said recording medium is magnetic tape.

13. The method of claim 9 further including the step of recording audio observations of an operator while manipulating said housing from exteriorly of said enclosed structure.

* * * * *